United States Patent [19]

Imada et al.

[11] Patent Number: 4,495,104
[45] Date of Patent: Jan. 22, 1985

[54] QUINONE CARBOXYLIC ACIDS AND ESTER DERIVATIVES

[75] Inventors: Isuke Imada, Izumi; Tetsuya Okutani, Takatsuki; Masazumi Watanabe, Kawanishi, all of Japan

[73] Assignee: Takeda Chemical Industries, Ltd., Osaka, Japan

[21] Appl. No.: 167,522

[22] Filed: Jul. 11, 1980

[30] Foreign Application Priority Data

Apr. 15, 1980 [JP] Japan ................... 55-49956

[51] Int. Cl.³ ............... C07C 66/00; C07C 69/95
[52] U.S. Cl. ................. 260/396 R; 260/408; 260/409; 260/410.9 R; 260/413; 260/418; 260/410.9 R; 514/826; 544/171; 560/138; 560/190; 560/254; 568/319; 568/337; 568/651
[58] Field of Search ............ 260/396 R; 424/305, 424/318

[56] References Cited

U.S. PATENT DOCUMENTS 3,728,363  4/1973  Morimoto et al. ............ 260/396 R
3,849,453  11/1974  Morimoto et al. ............ 260/396 R
3,957,836  5/1976  Morimoto et al. ............ 260/396 R
4,139,545  2/1979  Morimoto et al. ............ 260/396 R

*Primary Examiner*—Vivian Garner
*Attorney, Agent, or Firm*—Wenderoth, Lind & Ponack

[57] ABSTRACT

A compound of the general formula

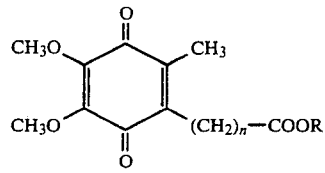

wherein n is an integer of 10 to 21, inclusive; R is H or lower alkyl having 1 to 4 carbon atoms has pharmaceutical activities such as hypotensive, tissue metabolism stimulating, immuno-regulatory, lysosomal membrane stabilizing and SRS-A production inhibitory activities and is useful as a heart failure remedy, cerebral circulation disturbance remedy, immuno-regulator, and antiallergic drug.

9 Claims, No Drawings

QUINONE CARBOXYLIC ACIDS AND ESTER DERIVATIVES

This invention relates to new quinone compounds of value as medicines and a method of producing the same compounds.

Ubiquinones are effective against heart failure, periodontal disease, diabetes, muscular dystrophy, asthma, etc. but because they are generally low in water solubility, the route of administration is limited and the onset of action is not satisfactory. The research undertaken by us resulted in the finding of new quinone compounds which are possessed of desirable pharmacological activities.

This invention is thus concerned with quinone compounds of the general formula

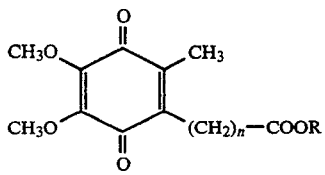

(wherein n is an integer of 10 to 21, preferably 13 to 18; R is H or lower alkyl] and a method of producing quinone compounds of general formula (I) which comprises:

(1) reacting a compound of the formula

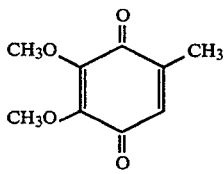

with a peroxide of a carboxylic acid of the general formula

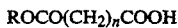

ROCO(CH$_2$)$_n$COOH (III)

[wherein R and n are respectively as defined above] or of an anhydride thereof [hereinafter referred to as Process (1) of this invention]; or (2) oxidizing a compound of the general formula

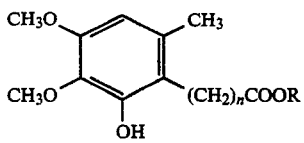

[wherein R and n are respectively as defined above] [hereinafter referred to as Process (2) of this invention]; or (3) oxidizing a compound of the general formula

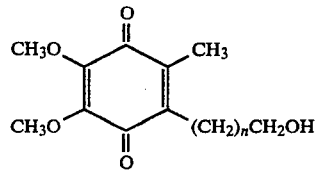

[wherein n is as defined above) and, if desired, esterifying the same [hereinafter referred to as Process (3) of this invention].

Referring to the above general formula (I), (III) and (IV), the lower alkyl group represented by R is an alkyl group of 1 to 4 carbon atoms, such as methyl, ethyl, n-propyl, i-propyl, n-butyl, i-butyl, t-butyl, etc.

Process (1) of this invention comprises reacting a compound (II) with a peroxide of compound (III) or of an anhydride thereof [hereinafter referred to sometimes as the peroxide compound (III′)]. The peroxide of compound (III′) may be any peroxide compound that, when heated, yields an alkyl radical with the evolution of carbon dioxide, and can be obtained for example by permitting hydrogen peroxide or its metal salt or lead tetracetate or the like to act upon the carboxylic acid or a halide or acid anhydride thereof.

Process (1) of this invention is preferably conducted in an appropriate inert solvent such as n-hexane, ligroin, toluene, xylene, acetic acid, propionic acid, etc. The molar ratio of compound (II) and the peroxide (III′) may usually be in the range of 1:1 to 1:2, preferably 1:1 to 1:1.5. The preferred reaction temperature is about 80° C. to 100° C. and the preferred reaction time is about 0.5 to 3 hours. This reaction proceeds under very mild conditions with evolution of carbon dioxide gas and with little side reactions, giving rise to the desired compound in good yield. Moreover, after the reaction the unreacted material can be fully recovered.

This reaction may be conducted under conditions such that the peroxide (III′) will be produced in the reaction system. Thus, for example, (II) may be reacted with (III′) ((III) or an anhydride thereof) in the presence of 1 to 2 mol of a tetravalent lead compound (e.g. lead tetracetate) relative to 1 mole of compound (II). This reaction is preferably carried out in an appropriate inert solvent (e.g. n-hexane, ligroin, toluene, xylene, acetic acid, propionic acid) and the preferred reaction temperature is 50° to 150° C.

The reaction according to Process (2) of this invention comprises oxidizing compound (IV). The oxidation method may be any of the methods by which generally phenol compounds can be converted to quinone. Specific examples of the oxidizing agent used for this reaction include ferric chloride, silver oxide, manganese dioxide, hydrogen peroxide, peracetic acid, performic acid, perbenzoic acid, potassium permanganate potassium dichromate, chromic anhydride, potassium nitrosodisulfonate, cobalt complex/oxygen, etc. This reaction is normally conducted in the presence of a suitable solvent. The solvent may be any solvent that will not interfere with the reaction, being exemplified by water, a dilute aqueous solution of acid or alkali, acetone, ethanol, dioxane, ether, acetic acid, halogenated hydrocarbons, N,N-dimethylformamide, hexamethylphosphoric triamide, etc. The progress of reaction can be monitored by thin-layer chromatography, where detection may be by a yellow spot, color reaction to leucomethylene blue, and UV absorption. The reaction temperature and time vary with different oxidizing agents but, normally, the reaction temperature is preferably from about 0° to 50° C. and the reaction time preferably from 0.5 hour to 10 days. Also, satisfactory results may be obtained by conducting the reaction in the presence of a suitable buffer (e.g. phosphate buffer).

Process (3) of this invention comprises oxidizing compound (V) and, if necessary, esterifying the same. The oxidation is effected by a procedure known per se. Thus, any method capable of converting the side-chain hydroxyl group to a carboxyl group can be employed. Preferred oxidizing agents are manganese dioxide, chromic acid, etc. This reaction may be carried out in the presence of a mineral acid, e.g. sulfuric acid, hydrochloric acid, etc. or a base, e.g. pyridine. This oxidation reaction yields compound (I) wherein R is H. When it is desired to obtain compound (I) wherein R is a lower alkyl group, the oxidation product compound is esterified. This esterification reaction may be effected for example by a method which comprises reacting a carboxylic acid or a reactive derivative in the carboxyl function thereof with an alcohol, phenol, alkyl halide, aralkyl halide, dialkyl sulfate or diazomethane. The reactive derivative of carboxylic acid includes the anhydride, halide, lower alkyl ester or metal salt (salts with sodium, potassium, silver, etc.) of the carboxylic acid. The alcohol may for example be methanol, ethanol, propanol, isopropyl alcohol, butanol, isobutyl alcohol, cyclohexylmethylcarbinol or the like, while the alkyl halide may for example be methyl iodide or ethyl iodie.

The compound (I) can thus be produced by Process (1), (2) or (3) of this invention.

When R is H in the compound (I) produced by Process (1) or (2) of this invention, the compound (I) may, if necessary, be converted to (I) wherein R is lower alkyl by the same procedure as the esterification reaction in Process (3) of this invention. When R of quinone (I) is lower alkyl, the compound may be hydrolyzed in the routine manner into quinone (I) wherein R is H. This hydrolysis reaction can be effected advantageously in the presence of a mineral acid (sulfuric acid, hydrochloric acid, etc.) or an alkaline substance (sodium hydroxide, potassium hydroxide, calcium hydroxide, etc.) The compound (I) wherein R is H may also be obtained by carrying out the hydrolysis reaction in the presence of a suitable antioxidant (e.g. pyrogallol) or a reducing agent (e.g. a hydrosulfite) and oxidizing the hydrolysate of general formula

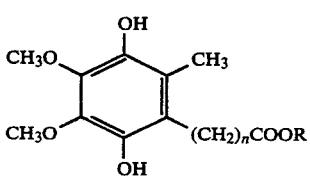

(VI)

[wherein R and n are as defined hereinbefore] with ferric chloride, silver oxide, air or the like.

The resultant quinone (I) can be easily isolated by suitable procedures known per se, such as pH adjustment, phase transfer, concentration, distillation under reduced pressure, chromatography, crystallization, recrystallization, etc.

When R of quinone (I) is a hydrogen atom, (I) may be isolated as a free carboxylic acid or as a pharmacologically acceptable salt. The free carboxylic acid, as isolated above, may be converted to such a salt. As examples of the salt may be mentioned alkali metal salts (sodium, potassium and other salts), alkaline earth metal salts (magnesium, calcium and other salts), ammonium and amine salts (e.g. trimethylamine, triethylamine and other salts).

The starting compound (IV) for Process (2) of this invention can be produced by subjecting compounds (VII) and (VIII) of the following formulas to Friedel-Crafts reaction to obtain compound (IX) and, then, reducing (IX).

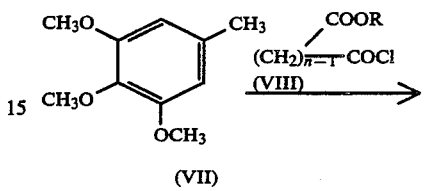

(VII)

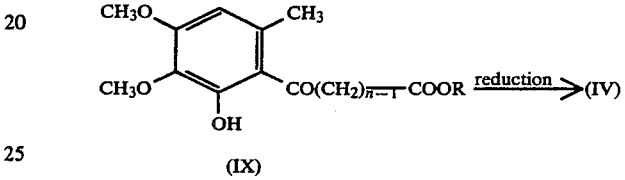

(IX)

[R and n in formulas (VIII) and (IX) are as defined hereinbefore]

The reaction between (VII) and (VIII) is preferably conducted in the presence of an appropriate catalyst which may be any Friedel-Crafts catalyst, such as mineral acids (e.g. sulfuric acid, phosphoric acid, polyphosphoric acid) and Lewis acids (e.g. aluminum chloride, boron trifluoride, etc.) to name some preferred examples. While the reaction proceeds in the absence of a solvent, it is normally carried out in an inert organic solvent such as nitrobenzene, carbon disulfide, dichloromethane, 1,2-dichloroethane, tetrachloroethane, etc. The reaction temperature is preferably about 0° to 150° C. The reduction of (IX) can be accomplished by any method that is capable of transforming the carbonyl group of (IX) to a methylene group. Preferred examples of said method are Clemmensen reduction with amalgamated zinc and hydrochloric acid, Wolff-Kishner reduction in which a ketone is converted to a hydrazone which is decomposed with a base, a method involving the formation of a dithioacetate and subsequent desulfurizing reduction with nickel catalyst (e.g. Raney nickel), catalytic reduction, and a method involving reduction to a hydroxyl group with sodium borohydride and subsequent catalytic reduction. It is normally preferable to conduct the above reaction in the presence of a suitable solvent which does not interfere with the reaction, such as ether, methanol, ethanol, benzene, toluene, xylene, ethylene glycol, triethylene glycol, acetic acid, etc. The above-mentioned reduction reaction can be easily carried out in the routine manner. By way of illustration, the catalytic reduction method is now described in detail. The catalyst may for example be palladium-on-carbon, platinum oxide, Raney nickel, rhodium-on-carbon or the like. The reaction solvent is preferably an acetic acid ester (e.g. ethyl acetate), an alcohol (e.g. methanol) or an organic acid (e.g. formic acid, acetic acid), for instance. This reduction reaction may be hastened by conducting it in the presence of hydrochloric acid, perchloric acid, p-toluene-sulfonic acid or the like. The reaction temperature is 0° to 150°

C.; normally the reaction is carried out at room temperature. The hydrogen pressure may range from 1 to 150 atmospheres and is preferably 1 atm.

The compound (IV) can also be produced by the following procedure.

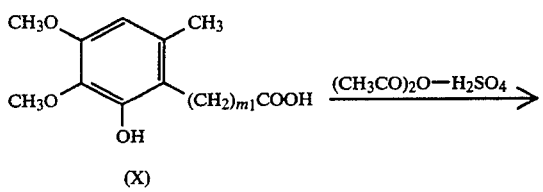
(X)

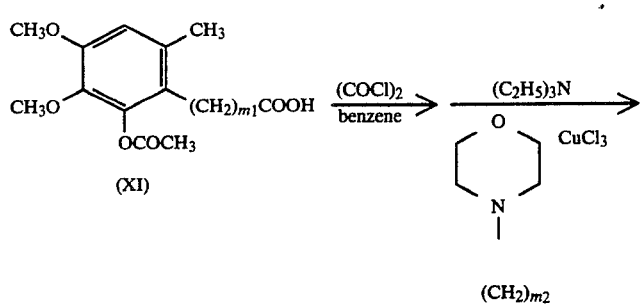
(XI)

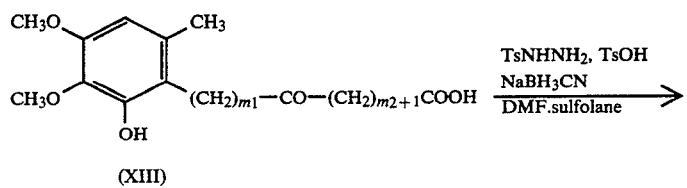
(XII)

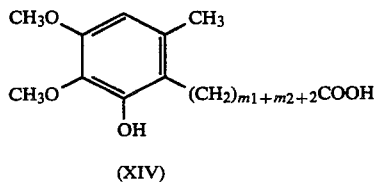
(XIII)

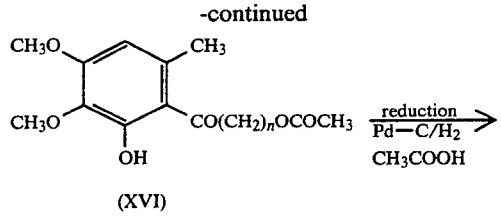
(XVI)

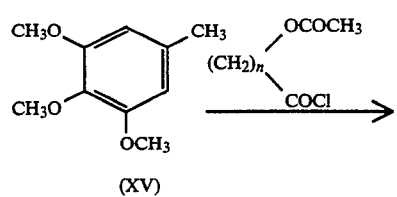
(XIV)

[wherein $m_2$ is an integer of 3 to 19; $m_1$ is an integer from 0 to 16, provided that $m_1+m_2$ is 8 to 19]

The starting compound (V) for Process (3) of this invention can be produced for example by the following procedure.

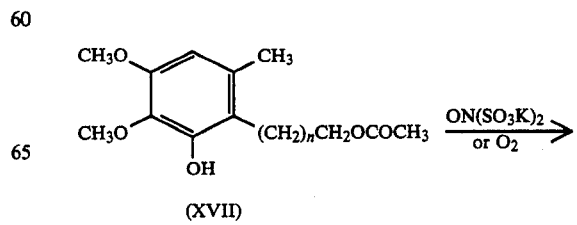
(XV)        (XVII)

-continued

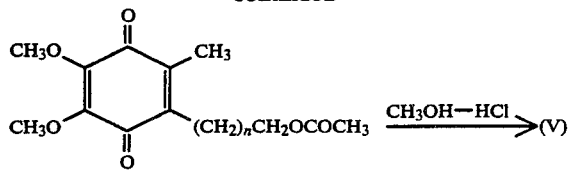

(n is as defined hereinbefore).

The present compound of general formula (I) has the physiological activity of ubiquinones and when the mitochondrial electron-transport activity of (I) was assayed by the general method for assaying the physiological activity of ubiquinones, it was found to display a marked degree of activity as shown in Table 1.

TABLE 1

| Compound | Electron-transport activity of the present compound[1] | |
|---|---|---|
| | Level of addition (n moles) | Succinate oxidase activity [oxygen consumption per mg enzyme protein during 1 minute (n atoms oxygen)] |
| Control | 0 | 19.34 ± 1.42 |
| [In formula I] n:12 R:H | 10 | 96.05 |
| [In formula I] n:12 R:CH₃ | 10 | 146.10 |
| [In formula I] n:17 R:H | 10 | 112.05 |

[1]Ubiquinone-depleted enzyme preparations were prepared in accordance with Lester and Fleischer (Biochem. Biophys. Acta., 47,358-377, 1961). The electron-transport activity was determined based on succinate oxidase activity.

Further, we investigated the effect of the present compound (I) on the production and release of the slow reacting substance of anaphylaxis (hereinafter, SRS-A) which has been mentioned as a main factor in asthma. Thus, in accordance with the method of Orange and Moore (J. Immunol., 116, 392-397, 1976), the present compound (I) was added to a quinea-pig lung fragments sensitized with egg albumin as the antigen, and the amount of SRS-A produced and released as a consequence was assayed by the method of Brocklehurst (J. Physiol., 151, 416-435, 1960). It was found that as shown in Table 2, the present compound displayed a very potent inhibitory action on SRS-A production at low concentration.

TABLE 2

The inhibitory effect of the present compound on SRS-A production

| Compound[1] [In formula I] | Concentration (μM) | Inhibitory effect on SRS-A production[2] (%) |
|---|---|---|
| R:H, n:12 | 1 | 60.0 ± 3.3 |
| | 10 | 87.2 ± 5.5 |
| R:H, n:17 | 10 | 82.8 ± 4.4 |
| R:H, n:21 | 10 | 80.5 ± 0.5 |

[1]The compound was added as dissolved in ethanol or dimethyl sulfoxide.
[2]The inhibitory effect on SRS-A production was expressed as the % inhibition of production and release of SRS-A.

The present compound (I) has hypotensive, tissue metabolism-stimulating, immuno-regulatory, lysosomal membrane stabilizing and SRS-A (slow reacting substance of anaphylaxis) production inhibitory activities and is used as a heart failure remedy, cerebral circulation disturbance remedy, immuno-regulator, antiallergic drug (for the treatment of e.g. asthma, rhinitis, etc.), etc. for mammalian animals including human beings. Useful dosage forms include capsules, granules, powders, tablets, troches, pills, syrup, injections, suppositories, etc. As an antiallergic drug, such dosage forms as ointment, aerosol, inhalation mist, etc. may be employed.

The pharmaceutically acceptable materials which can be used in formulating pharmaceutical preparations include, among others, excipients such as sucrose, lactose, glucose, starch, mannitol, sorbitol, cellulose, talc, cyclodextrin, etc.; binders such as cellulose, methylcellulose, polyvinyl pyrrolidone, gelatin, gum arabic, polyethylene glycol, sucrose, starch, etc.; disintegrators such as starch, carboxymethylcellulose, carboxymethylcellulose calcium salt, etc.; lubricants such as talc; flavorants; preservatives such as sodium benzoate; suspending agents such as methylcellulose, polyvinyl pyrrolidone, aluminum stearate, Polysorbate 80, Emalgen 408, Emasol 310, etc., solvents such as water, and such pharmaceutical bases as cacao butter, polyethylene glycol, witepsol, white petrolatum, etc. These materials are selectively used according to the type of pharmaceutical preparation.

The compound (I) of this invention is administered orally or otherwise, at doses of 5 to 500 mg, preferably 10 to 300 mg, daily (0.1 to 10 mg/kg) for adult humans, for instance.

EXAMPLE 1

In 20 ml of acetic acid is dissolved 1.7 g of 2,3-dimethoxy-5-methyl-1,4-benzoquinone, and under stirring at 90° C., 7.6 g of bis-13-methoxycarbonyltridecanoyl peroxide is added in small portions. The mixture is heated for 22 hours and, after cooling, is diluted with water and extracted with ether. The extract is washed with a saturated aqueous solution of sodium chloride, aqueous sodium hydrogen carbonate and aqueous sodium chloride in that order, followed by drying. The solvent is distilled off under reduced pressure and the residue is recrystallized from hexane to obtain 1.37 g of 2,3-dimethoxy-6-(12-methoxycarbonyldodecyl)-5-methyl-1,4-benzoquinone (I:n=12, R=CH₃). m.p. 54° C.

Elemental analysis for $C_{23}H_{36}O_6$. Calcd. C, 67.62; H, 8.88. Found C, 67.52; H, 8.59.

EXAMPLE 2

In 200 ml of ether is dissolved 1.5 g of 2,3-dimethoxy-6-(12-methoxycarbonyldodecyl)-5-methyl-1,4-benzoquinone (I:n=12, R=CH₃) and the solution is shaken with 75 ml of a 20% aqueous solution of sodium hydrosulfite. The ether layer is separated and concentrated. To the residue are added, under ice-cooling and in a nitrogen gas stream, 5 ml of a 30% aqueous solution of sodium hydrosulfite and 3.5 ml of a 30% aqueous solution of potassium hydroxide. The mixture is warmed at 50° C. for 2.5 hours. After cooling, the reaction mixture is made acidic with cold hydrochloric acid and extracted with ether. The ether is distilled off under reduced pressure, the residue dissolved in 75 ml of methanol and a solution of 15 g of ferric chloride in 60 ml of water added. The mixture is stirred at room temperature for 1 hour, at the end of which time it is diluted with water and extracted with ethyl acetate. The extract is washed with water and dried, and the solvent is distilled off under reduced pressure. The residue is crystallized from ether-hexane to obtain 1.09 g of 6-(12-carboxydodecyl)-2,3-dimethoxy-5-methyl-1,4-benzoquinone (I:n=12, R=H), m.p. 62° C.

Elemental analysis for $C_{22}H_{34}O_6$. Calcd. C, 66.98; H, 8.69 Found C, 67.15; H, 8.77.

EXAMPLE 3

To a solution of 300 mg of 22-(2-hydroxy-3,4-dimethoxy-6-methylphenyl)docosanoic acid (IV:n=21, R=H) in 20 ml of N,N-dimethylformamide is added 50 mg of bis(salicylidene)ethylenediiminocobalt(II) and the mixture is stirred in oxygen gas stream at room temperature for 24 hours. The insolubles are filtered off and the filtrate is concentrated under reduced pressure. The residue is dissolved in ethyl acetate, washed with water and dried. The solvent is distilled off and the residue is dissolved in chloroform and column-chromatographed on silica gel, elution being carried out with chloroform. The eluate is recrystallized from ethanol to obtain 6-(21-carboxyheneicosyl)-2,3-dimethoxy-5-methyl-1,4-benzoquinone (I:n=21, R=H) as orange-yellow needles melting at 86° C.–87° C.

Elemental analysis for $C_{31}H_{52}O_6$. Calcd. C, 71.50; H, 10.07. Found C, 71.56; H, 10.06.

EXAMPLE 4

In 10 ml of acetone is dissolved 172 mg of 6-(18-hydroxyoctadecyl)-2,3-dimethoxy-5-methyl-1,4-benzoquinone (V:n=17). Separately, 2.672 g of chromic anhydride is dissolved in 2.3 ml of concentrated sulfuric acid and diluted with water to 10 ml. This diluted solution (0.5 ml) is added to the above acetone solution and the mixture is stirred under ice-cooling for 10 minutes. The reaction mixture is diluted with water and extracted with chloroform. The extract is washed with water and dried, and the solvent is distilled off under reduced pressure. The residue is column-chromatographed on silica gel, elution is carried out with chloroform and the eluate is recrystallized from ethanol. The above procedure yields 65 mg of 6-(17-carboxyheptadecyl)-2,3-dimethoxy-5-methyl-1,4-benzoquinone (I:n=17, R=H) as orange-yellow crystals, m.p. 77°–79° C.

Elemental analysis for $C_{27}H_{44}O_6$. Calcd. C, 69.79; H, 9.55. Found C, 69.86; H, 9.78.

EXAMPLE 5

6-(11-Hydroxyundecyl)-2,3-dimethoxy-5-methyl-1,4-benzoquinone (V:n=10) is reacted in the same manner as in Example 4 and the product is purified by silica gel column chromatography to recover orange-yellow needles of 6-(10-carboxydecyl)-2,3-dimethoxy-5-methyl-1,4-benzoquinone (I:n=10, R=H), m.p. 50° C.–52° C.

NMR (δ, in deuteriochloroform): 1.32(16H,b,$CH_2$), 2.03(3H,s,$CH_3$), 2.18–2.65(4H,m,$CH_2COO$, $CH_2$ on the ring), 4.02(6H,s,$OCH_3$), 5.35(1H,b,COOH).

EXAMPLE 6

In dimethylformamide (20 ml) is dissolved 16-(2-hydroxy-3,4-dimethoxy-6-methylphenyl)hexadecanoic acid (IV:n=15, R=H) (844 mg), followed by addition of bis(salicylidene)ethylenediiminocobalt(II) (163 mg). The mixture is stirred in a stream of oxygen gas at room temperature for 24 hours. The solvent is distilled off, the residue dissolved in ethyl acetate (100 ml) and the insolubles are filtered off. The filtrate is washed with 1N—HCl and water and dried over anhydrous sodium sulfate. The solvent is distilled off and the residue is dissolved in a small amount of chloroform and purified by column chromatography on silica gel (20 g) with chloroform as the eluent. The fractions containing the product compound are pooled, the solvent is distilled off and the residue is recrystallized from ether-petroleum ether to obtain 514 mg of 6-(15-carboxypentadecyl)-2,3-dimethoxy-5-methyl-1,4-benzoquinone (I:n=15, R=H), m.p. 70° C.–71° C.

Elemental analysis for $C_{25}H_{40}O_6$. Calcd. C, 68.77; H, 9.23. Found C, 68.89; H, 9.30.

Reference Example 1

In 200 ml of petroleum ether is dissolved 11.7 g of methyl 13-chloroformyltridecanoate, and under ice-cooling and stirring, 60 ml of ice-water is added, followed by addition of 5.2 g of sodium peroxide in small portions. The mixture is stirred for an hour, at the end of which time it is extracted with ether. The extract is washed with water and dried over calcium chloride, and the solvent is distilled off under reduced pressure. The above procedure yields 7.6 g crude crystals of bis-13-methoxycarbonyltridecanoyl peroxide. This product is subjected to the next reaction without being purified. $IR\nu_{max}^{film}cm^{-1}$: 1790, 1760

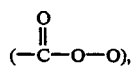

1730 ($COOCH_3$).

Reference Example 2

To a solution of 11-acetoxy-n-undecanoyl chloride (27.6 g) in 1,2-dichloroethane (150 ml) is added aluminum chloride (28 g) and the mixture is stirred at room temperature for 2 hours. The reaction mixture is cooled to 5° C. and, then, a solution of 3,4,5-trimethoxytoluene (19.1 g) in 1,2-dichloroethane (50 ml) is added. The mixture is stirred at room temperature for 72 hours. The reaction mixture is heated to 50° C.–60° C. and further stirred for 30 minutes. After cooling, 300 ml of ice-water is added to the reaction mixture and the product is extracted with dichloromethane. The dichloromethane layer is washed with water and dried over anhydrous magnesium sulfate. The solvent is then distilled off to recover 6-(11-acetoxy-1-oxoundecyl)-2,3-dimethoxy-5-methylphenol (35 g).

$IR\nu_{max}^{Neat}cm^{-1}$: 1730(OAc), 1680(CO), 1610, 1580(Ar). MS m/e: 394($M^+$), 352, 334, 195.

Sodium hydroxide (7 g) is added to a solution of 6-(11-acetoxy-1-oxoundecyl)-2,3-dimethoxy-5-methylphenol (34 g) in methanol (300 ml) and the mixture is stirred at room temperature for 2 hours. To the reaction mixture is neutralized with 5N—HCl and the solvent is distilled off, whereupon crude crystals are obtained. These crystals are rinsed with water and recrystallized from ether-hexane (1:1). The above procedure yields colorless needles of 6-(11-hydroxy-1-oxoundecyl)-2,3-dimethoxy-5-methylphenol (30 g), m.p. 81° C.

Elemental analysis for $C_{20}H_{32}O_5$. Calcd. C, 68.15; H, 9.15. Found C, 68.47; H, 9.30.

To a solution of 6-(11-hydroxy-1-oxoundecyl)-2,3-dimethoxy-5-methylphenol (14 g) in acetic acid (200 ml) are added 5% palladium-on-carbon (50% hydrous) (3 g) and 70% perchloric acid (0.1 ml), and catalytic reduction is carried out at atmospheric temperature and pressure. When the hydrogen has ceased to be absorbed, the catalyst is filtered off and the filtrate is concentrated under reduced pressure. The residue is extracted with dichloromethane and the dichloromethane layer is washed with a 5% aqueous solution of sodium hydrogen carbonate and dried over anhydrous magnesium sulfate. The solvent is then distilled off to obtain a colorless oil of 6-(11-acetoxyundecyl)-2,3-dimethoxy-5-methylphenol (15 g).

IR$\nu_{max}^{Neat}$cm$^{-1}$: 3450(OH), 1730(OAc), 1610, 1580(Ar). NMR$\delta_{ppm}^{CDCl_3}$: 1.1–1.9[18H,m,—(CH$_2$)$_9$—], 2.02(3H,s,OAc), 2.22(3H,s,C$_5$—CH$_3$), 2.54(2H,t,J=7 Hz,C$_1$—H$_2$ of side chain), 3.79(3H,s,OCH$_3$), 3.83(3H,s,OCH$_3$), 4.01(2H,t,J=6 Hz,—CH$_2$OAc), 5.78(1H,s,C$_1$—OH), 6.23(1H,s,C$_4$—H).

MS m/e: 380(M$^+$), 338, 181.

To a solution of 6-(11-acetoxyundecyl)-2,3-dimethoxy-5-methylphenol (8 g) in N,N-dimethylformamide (400 ml) are added potassium nitrosodisulfonate (24 g), water (400 ml), methanol (30 ml) and monopotassium phosphate (1.0 g). The mixture is stirred at room temperature for 28 days. The product is extracted with dichloromethane and the dichloromethane layer is washed with water and dried over anhydrous magnesium sulfate. The solvent is then distilled off and the resultant crude crystals are recrystallized from hexane. The above procedure yields 6-(11-acetoxyundecyl)-2,3-dimethoxy-5-methyl-1,4-benzoquinone (6.4 g) as orange-yellow needles, m.p. 41° C.

Elemental analysis for C$_{22}$H$_{34}$O$_6$. Calcd. C, 66.98; H, 8.69. Found C, 66.98; H, 8.86.

To a solution of 6-(11-acetoxyundecyl)-2,3-dimethoxy-5-methyl-1,4-benzoquinone (4.2 g) in methanol (200 ml) is added concentrated hydrochloric acid (0.1 ml) and the mixture is allowed to stand at room temperature for 12 hours.

To the reaction mixture is added sodium hydrogen carbonate (0.2 g) and the solvent is distilled off. The product is dissolved in dichloromethane, the insolubles are filtered off and the dichloromethane is distilled off. The resultant crude crystals are recrystallized from hexane-ether (3:1) to obtain 6-(11-hydroxyundecyl)-2,3-dimethoxy-5-methyl-1,4-benzoquinone (V:n=10) as orange-colored needles (3.6 g), m.p. 57° C.

Elemental analysis for C$_{20}$H$_{32}$O$_5$. Calcd. C, 68.15; H, 9.15. Found C, 68.22; H, 9.19.

Reference Example 3

To a solution of 18-acetoxy-n-octadecanoyl chloride (11 g) in 1,2-dichloroethane (50 ml) is added aluminum chloride (7 g) and the mixture is stirred at room temperature for 2 hours. This reaction mixture is cooled to 5° C. and a solution of 3,4,5-trimethoxytoluene (6.2 g) in 1,2-dichloroethane (20 ml) is added. The mixture is stirred at room temperature for 72 hours. Then, this reaction mixture is heated to 50° C.–60° C. and stirred for 30 minutes. After cooling, ice-water is added to the reaction mixture and the product is extracted with dichloromethane. The dichloromethane layer is washed with water and the solvent is distilled off to recover an oil (12.1 g). This oil is dissolved in methanol (150 ml) followed by addition of sodium hydroxide (5.2 g). The mixture is stirred at room temperature for 2 hours, at the end of which time it is neutralized with 5N—HCl and the solvent is distilled off. The resultant crude crystals are rinsed with water and recrystallized from dichloromethane-ether (1:1). The above procedure yields 6-(18-hydroxy-1-oxooctadecyl)-2,3-dimethoxy-5-methylphenol (6.4 g) as colorless needles, m.p. 101° C.

Elemental analysis for C$_{27}$H$_{46}$O$_5$. Calcd. C, 71.96; H, 10.29. Found C, 72.08; H, 10.51.

To a solution of 6-(18-hydroxy-1-oxooctadecyl)-2,3-dimethoxy-5-methylphenol (1.4 g) in acetic acid (30 ml) are added 5% palladium-on-carbon (50% hydrous) (0.5 g) and 70% perchloric acid (0.05 ml), and catalytic reduction is carried out at atmospheric temperature and pressure. After the absorption of hydrogen has subsided, the catalyst is filtered off and the filtrate is concentrated under reduced pressure, whereupon a colorless oil is obtained. This product is dissolved in ether and the ether layer is washed with 5% aqueous solution of sodium hydrogen carbonate and dried over anhydrous sodium sulfate. The solvent is then distilled off and the resultant crude crystals are recrystallized from hexane. The above procedure yields 6-(18-acetoxyoctadecyl)-2,3-dimethoxy-5-methylphenol (1.4 g) as colorless needles, m.p. 53° C.

Elemental analysis for C$_{29}$H$_{50}$O$_5$. Calcd. C, 72.76; H, 10.53. Found C, 73.05; H, 10.31.

The above 18-acetoxy compound was deacetylated by the corresponding procedure of Reference Example 2 and the resultant 6-(18-hydroxyoctadecyl)-2,3-dimethoxy-5-methylphenol (0.5 g) is dissolved in dimethylformamide (1 l). To this solution is added potassium nitrosodisulfonate (13 g), 700 ml of water, 100 ml of methanol and monopotassium phosphate (1 g), and the mixture is stirred at room temperature for 45 days. The product is extracted in the conventional manner and recrystallized from ether-hexane. The above procedure yields 6-(18-hydroxyoctadecyl)-2,3-dimethoxy-5-methyl-1,4-benzoquinone (V, n=17) as yellow needles (0.31 g), m.p. 81° C.

Elemental analysis for C$_{27}$H$_{46}$O$_5$. Calcd. C, 71.96; H, 10.29. Found C, 72.06; H, 10.27.

Reference Example 4

In 5 ml of thionyl chloride is dissolved 1 g of monomethyl 1,20-eicosanedicarboxylate, and after stirring at room temperature for 12 hours, the excess thionyl chloride is distilled off to recover crude crystals of methyl 21-chloroformylheneicosanoate. This product is subjected to the next reaction without being purified. IR$\nu_{max}^{KBr}$cm$^{-1}$: 1790(COCl), 1730(COOCH$_3$).

In 60 ml of 1,2-dichloroethane is dissolved 8 g of methyl 21-chloroformylheneicosanoate, followed by addition of 5.5 g of aluminum chloride. The mixture is stirred. Then, under ice-cooling and stirring in a nitrogen stream, a solution of 5.67 g of 3,4,5-trimethoxytoluene in 1,2-dichloroethane (13 ml) is added dropwise. The mixture is stirred for 48 hours, after which 1.3 g of aluminum chloride is added. The mixture is stirred at room temperature for 16 hours and further at 35° C.–38° C. for 40 minutes. To this reaction mixture are added ice-water and 3N-HCl, followed by extraction with chloroform. The extract is washed with water, a saturated aqueous solution of sodium hydrogen carbonate and water in that order. After drying, the solvent is distilled off under reduced pressure and the residue is chromatographed on silica gel. The fractions containing the desired compound are pooled and recrystallized from methanol. The above procedure yields methyl 21-(2-hydroxy-3,4-dimethoxy-6-methylbenzoyl)-heneicosanoate as colorless needles. m.p. 73°–74° C. NMR(δ, in deuteriochloroform): 1.24(36H, b, CH$_2$), 2.27(2H,t,CH$_2$COO), 2.42(3H, s, nuclear CH$_3$), 2.86(2H, t,COCH$_2$), 3.64(3H,s,COOCH$_3$), 3.84(3H,s,OCH$_3$), 3.87(3H,s,OCH$_3$), 6.22(1H,s,nuclear H).

To a solution of methyl 21-(2-hydroxy-3,4-dimethoxy-6-methylbenzoyl)heneicosanoate in acetic acid is added perchloric acid and catalytic reduction is carried out with 5% palladium-on-carbon. The reaction mixture is worked up as in the corresponding step of Reference Example 2 and the resultant product is recrystallized from ethanol. The above procedure yields methyl 22-(2-hydroxy-3,4-dimethoxy-6-methylphenyl)-docosanoate as colorless needles, m.p. 71° C.-72.5° C.

Elemental analysis for $C_{32}H_{56}O_5$. Calcd. C, 73.80; H, 10.84. Found C, 74.06; H, 11.06.

In 15 ml of methanol is dissolved 300 mg of methyl 22-(2-hydroxy-3,4-dimethoxy-6-methylphenyl)-docosanoate followed by addition of 20 ml of a 14% aqueous solution of sodium hydroxide. The mixture is stirred at 50°-60° C. for 1.5 hours. The reaction mixture is made acidic with 3N—HCl and extracted with ethyl acetate. The extract is washed with water and, after drying, the solvent is distilled off under reduced pressure. The residue is recrystallized from methanol to obtain 22-(2-hydroxy-3,4-dimethoxy-6-methylphenyl)-docosanoic acid (IV:n=21), m.p. 67° C.–68° C. NMR($\delta$, in deuteriochloroform): 1.27(38H,b,$CH_2$), 2.24(3H,s,nuclear $CH_3$), 2.28-2.56(4H,m,$CH_2COO$, nuclear $CH_2$), 3.80(3H,s,$OCH_3$), 3.84(3H,s,$OCH_3$), 6.24(1H,s, nuclear H)

Reference Example 5

In acetic anhydride (100 ml) is suspended 10-(2-hydroxy-3,4-dimethoxy-6-methylphenyl)decanoic acid (33.8 g) followed by addition of concentrated sulfuric acid (5 ml). The mixture is reacted at room temperature for 1.5 hours, at the end of which time the solvent is distilled off. To the residue are added dioxane (250 ml) and a 5% aqueous solution of sodium hydrogen carbonate (250 ml), and the mixture is stirred at room temperature for 24 hours. The reaction mixture is adjusted to pH 3 with 6N—HCl and extracted by the addition of ethyl acetate (300 ml) and water (500 ml). The ethyl acetate layer is washed with water and dried over anhydrous sodium sulfate. The solvent is distilled off to recover 36.2 g of 10-(2-acetoxy-3,4-dimethoxy-6-methylphenyl)decanoic acid as oil. This oil is dissolved in anhydrous benzene (50 ml), and under ice-cooling, oxalyl chloride (25 ml) is added dropwise. Following the dropwise addition and after bubbles have subsided, the reaction is allowed to proceed at 50° C. for an hour. The solvent is then distilled off, toluene is added and the solvent is distilled off under reduced pressure. The residue is dried over sodium hydroxide in a desiccator to obtain 36.9 g of 6-(9-chloroformylnonyl)-2,3-dimethoxy-5-methylphenyl acetate. NMR($\delta$, in deuteriochloroform): 1.33(14H, b, $CH_2$), 2.33, 2.37(6H, s, $COCH_3$, nuclear $CH_3$), 2.95(4H, t, $CH_2CO$, nuclear $CH_2$), 3.87, 3.90(6H, s, $OCH_3$), 6.73(1H, s, nuclear H). $IR\nu_{max}^{film} cm^{-1}$: 1800(COCl), 1770(OCOCH_3).

In chloroform (4 ml) is dissolved 6-(9-chloroformylnonyl)-2,3-dimethoxy-5-methylphenyl acetate (5.0 g), and under ice-cooling, the solution is added dropwise to a mixture of 1-morpholino-1-cyclohexene (2.51 g) and triethylamine (1.93 ml). After the dropwise addition has been completed, the reaction is allowed to proceed at room temperature for 90 hours. To this reaction mixture is added 6N-hydrochloric acid (7.5 ml), and with vigorous stirring, the mixture is refluxed for 5 hours. The mixture is subjected to extraction by the addition of chloroform (20 ml) and water (20 ml). The water layer is further extracted with chloroform (20 ml) and the chloroform layers are combined, washed with water and dried over anhydrous sodium sulfate. The solvent is distilled off and the residue is dissolved again in chloroform and subjected to chromatography on silica gel (60 g), elution being carried out with chloroform. The fractions containing the desired compound are pooled and the solvent is distilled off to obtain 3.2 g of 2-[10-(2-acetoxy-3,4-dimethoxy-6-methylphenyl)decanoyl]cyclohexanone as oil. This oil is dissolved in ethanol (3.5 ml) followed by addition of a hot 6N-aqueous solution of sodium hydroxide (3.5 ml). The mixture is heated under reflux for 10 minutes. Then, at room temperature, the reaction mixture is adjusted to pH 2 with 6N—HCl, followed by extraction by the addition of ethyl acetate (30 ml) and water (30 ml). The water layer is further extracted with ethyl acetate (10 ml) and the ethyl acetate layers are combined, washed with water and dried over anhydrous sodium sulfate. The solvent is distilled off and the residue is recrystallized from ether-petroleum ether. The above procedure yields 1.96 g of 7-oxo-16-(2-hydroxy-3,4-dimethoxy-6-methylphenyl)-hexadecanoic acid, m.p. 55° C.–57° C.

Elemental analysis for $C_{25}H_{40}O_6$. Calcd. C, 68.77; H, 9.73. Found C, 68.64; H, 9.40.

To a solvent mixture of dimethylformamide (10 ml) and sulfolane (10 ml) containing p-toluenesulfonic acid (100 mg) is added 7-oxo-16-(2-hydroxy-3,4-dimethoxy-6-methylphenyl)hexadecanoic acid (1.75 g) and p-toluenesulfonyl hydrazide (930 mg) at 100° C. After 5 minutes, cyclohexane (10 ml) and sodium cyanoborohydride (1.0 g) are added. The reaction is conducted at 100° C. for 20 minutes. Then, at room temperature, a saturated aqueous solution of sodium chloride (100 ml) is added, followed by extraction with ether (50 ml×2). The ether layers are combined, washed with water, 1N—HCl and water in that order, and dried over anhydrous sodium sulfate. The solvent is distilled off, and the residue is dissolved in chloroform and subjected to column chromatography on silica gel, elution being carried out with chloroform. The fractions containing the desired compound are pooled and the solvent is distilled off. To the crystalline residue is added petroleum ether and, after cooling, the crystals are collected by filtration. The above procedure yields 970 mg of 16-(2-hydroxy-3,4-dimethoxy-6-methylphenyl)hexadecanoic acid, m.p. 45° C.–46° C.

Elemental analysis for $C_{25}H_{42}O_5$. Calcd. C, 71.05; H, 10.02. Found C, 71.13; H, 10.13.

Reference Example 6

(1) In the presence of triethylamine (14.3 ml), 6-(9-chloroformylnonyl)-2,3-dimethoxy-5-methylphenyl acetate (36.9 g) is reacted with 1-morpholino-1-cyclododecene (24.3 g) as in the corresponding step of Reference Example 5. The reaction product is treated with 6N—HCl (47 ml) and the resultant 2-[10-(2-acetoxy-3,4-dimethoxy-6-methylphenyl)decanoyl]cyclododecanone (46.3 g) is hydrolyzed with a 6N-aqueous solution of sodium hydroxide to obtain 32.4 g of 13-oxo-22-(2-hydroxy-3,4-dimethoxy-6-methylphenyl)docosanoic acid, m.p. 63°-64° C.

Elemental analysis for $C_{31}H_{52}O_6$. Calcd. C, 71.50; H, 10.07. Found C, 71.57; H, 10.17.

(2) 13-oxo-22-(2-hydroxy-3,4-dimethoxy-6-methylphenyl)docosanoic acid (5.21 g) is reduced in the presence of p-toluenesulfonic acid (250 mg) and p-toluenesulfonyl hydrazide (2.33 g) in a solvent mixture of dimethylformamide (25 ml)-sulfolane (25 ml)- cyclohexane (25 ml) as in the corresponding step of Reference Example 5. The resultant crude product is recrystallized from methanol to obtain 2.97 g of 22-(2-hydroxy-3,4-dimethoxy-6-methylphenyl)docosanoic acid, m.p. 67° C.–68° C. The physico-chemical constants of this product are all in agreement with those of the crystals obtained in Reference Example 4.

Elemental analysis for $C_{31}H_{54}O_5$. Calcd. C, 73.47; H, 10.74. Found C, 73.76; H, 10.78.

What is claimed is:

1. A compound of the formula

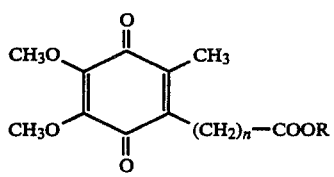

wherein n is an integer of 10 to 21, inclusive, and R is hydrogen or alkyl having 1 to 4 carbon atoms.

2. A compound as claimed in claim 1, wherein R is hydrogen.

3. A compound as claimed in claim 1, wherein R is an alkyl having 1 to 4 carbon atoms.

4. A compound as claimed in claim 1, wherein n is an integer of 13 to 18.

5. A compound as claimed in claim 1, wherein the compound is 2,3-dimethoxy-6-(12-methoxycarbonyldodecyl)-5-methyl-1,4-benzoquinone.

6. A compound as claimed in claim 1, wherein the compound is 6-(21-carboxyheneicosyl)-2,3-dimethoxy-5-methyl-1,4-benzoquinone.

7. A compound as claimed in claim 1, wherein the compound is 6-(17-carboxyheptadecyl)-2,3-dimethoxy-5-methyl-1,4-benzoquinone.

8. A compound as claimed in claim 1, wherein the compound is 6-(12-carboxydodecyl)-2,3-dimethoxy-5-methyl-1,4-benzoquinone.

9. A compound as claimed in claim 1, wherein the compound is 6-(15-carboxypentadecyl)-2,3-dimethoxy-5-methyl-1,4-benzoquinone.

* * * * *